US00PP32337P2

(12) United States Plant Patent
Holtmaat

(10) Patent No.: US PP32,337 P2
(45) Date of Patent: Oct. 13, 2020

(54) ***ECHINACEA* PLANT NAMED 'STRAWBERRY AND CREAM'**

(50) Latin Name: ***Echinacea* hybrid**
Varietal Denomination: Strawberry and Cream

(71) Applicant: AB-Kwekersrechten BV, Zuidwolde (NL)

(72) Inventor: Henricus Maria Joseph Holtmaat, Zuidwolde (NL)

(73) Assignee: AB-KWEKERSRECHTEN BV, Zuidwolde (NL)

( * ) Notice: Subject to any disclaimer, the term of this patent is extended or adjusted under 35 U.S.C. 154(b) by 0 days.

(21) Appl. No.: 16/501,672

(22) Filed: May 20, 2019

(30) Foreign Application Priority Data

Mar. 13, 2019 (QZ) ..... PBR 2019/0683

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./263.1, 428
See application file for complete search history.

(56) References Cited

PUBLICATIONS

AB Cultivar website (https://www.ab-cultivars.com/?portfolio=echinacea-strawberry-cream). Retrieved Feb. 10, 2020. 6 pages. (Year: 2018).*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of hybrid *Echinacea* plant named 'Strawberry and Cream' that is characterized by its inflorescences with ray florets that are pale yellow-green in color with red bases, its conspicuous multicolored disk florets, and its strong flowering stems, and its strong and vigorous growth habit.

2 Drawing Sheets

Botanical classification: *Echinacea* hybrid.
Variety denomination: 'Strawberry and Cream'.

BACKGROUND OF THE INVENTION

The present invention relates to a new and distinct cultivar of *Echinacea* of hybrid origin and will be referred to hereafter by its cultivar name 'Strawberry and Cream'. 'Strawberry and Cream' is an herbaceous perennial grown for landscape and container use.

The new invention arose from an ongoing controlled breeding program in Zuidwolde, The Netherlands. The objective of the breeding program was to develop cultivars of *Echinacea* with unique flower colors and sturdy plant habits with enlarged disk florets.

The Inventor discovered the new cultivar as a chance seedling in July of 2017 in a trial field that was planted with seeds collected from numerous cultivars and proprietary plants. The parent plants are therefore unknown.

Asexual propagation of the new cultivar was first accomplished under the direction of the Inventor by tissue culture using meristem tissue in March 2018 in Heerhugowaard, The Netherlands. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Strawberry and Cream' as unique cultivar of *Echinacea*.

1. 'Strawberry and Cream' exhibits inflorescences with ray florets that are pale yellow-green in color with red bases.
2. 'Strawberry and Cream' exhibits conspicuous multicolored disk florets.
3. 'Strawberry and Cream' exhibits a strong and vigorous growth habit.

'Strawberry and Cream' can be most closely compared to the *Echinacea* cultivars 'Strawberry Shortcake' (not patented) and 'Guava Ice' (U.S. Plant Pat. No. 23,473). 'Strawberry Shortcake' is similar to 'Strawberry and Cream' in having inflorescences with bi-colored ray florets. 'Strawberry Shortcake' differs from 'Strawberry and Cream' in having a much smaller plant height, narrower leaves, and in having inflorescences with ray florets that are white in color with red-purple bases. 'Guava Ice' is similar to 'Strawberry and Cream' in having a strong growth habit and enlarged disk florets. 'Guava Ice' differs from 'Strawberry and Cream' in having a much smaller plant height and in having inflorescences with ray florets that are orange to pinkish orange in color.

BRIEF DESCRIPTION OF THE DRAWINGS

The accompanying colored photographs illustrate the overall appearance and distinct characteristics of the new *Echinacea*. The photographs were taken of ten-month-old plants of the new cultivar grown outdoors in a 17-cm container in Zuidwolde, The Netherlands.

The photograph in FIG. 1 illustrates the overall habit and appearance of 'Strawberry and Cream' in bloom.

Figure 1:
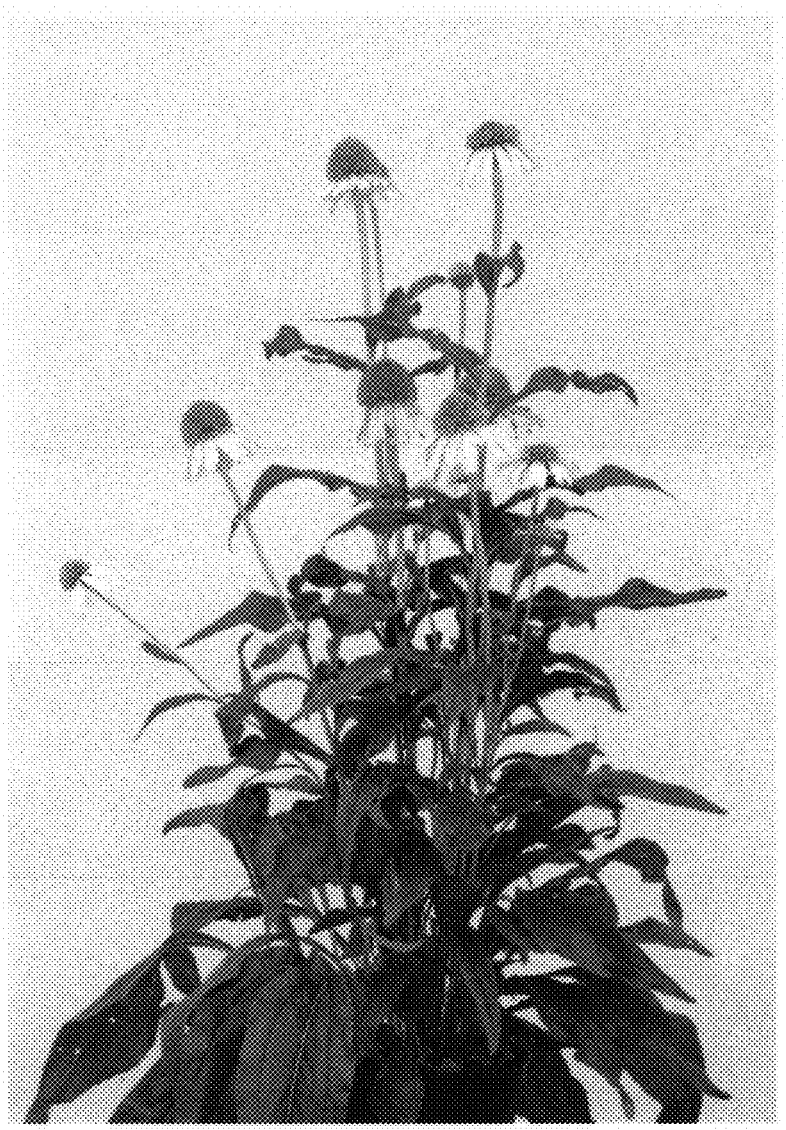
Figure 2:
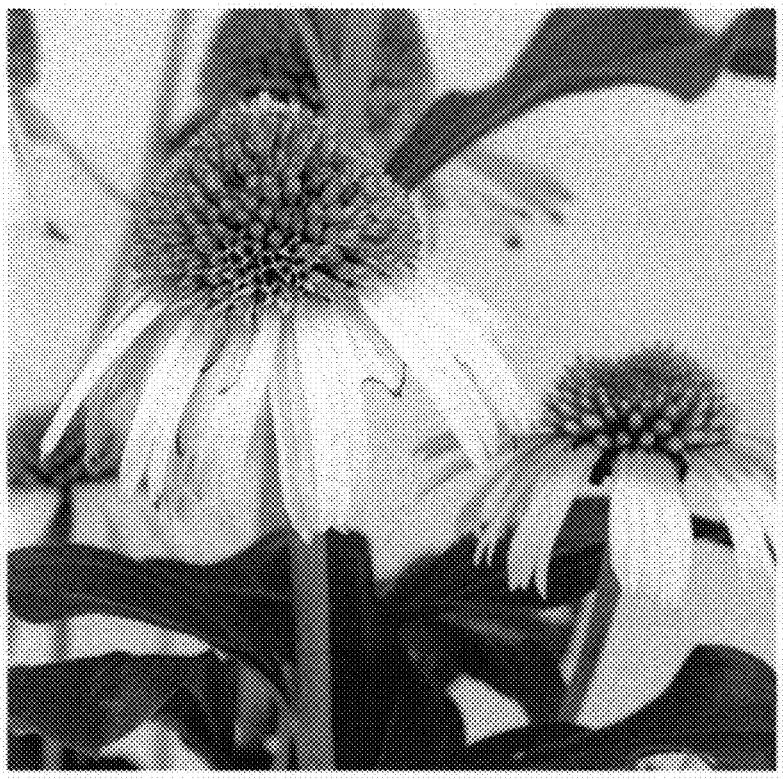

The photograph in FIG. 2 provides a close-up view of the inflorescences of 'Strawberry and Cream'.

Figure 3:
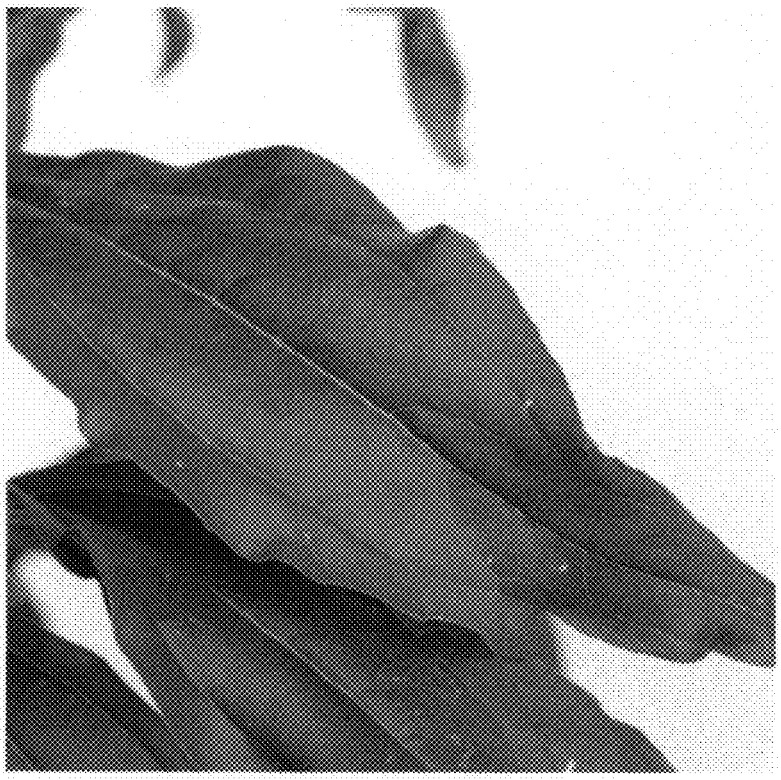

The photograph in FIG. 3 provides a close-up view of the foliage of 'Strawberry and Cream'.

The colors in the photographs are as close as possible with the photographic and printing technology utilized and color values cited in the detailed botanical description accurately describe the colors of the new *Echinacea*.

DETAILED BOTANICAL DESCRIPTION

The following is a detailed description of ten-month-old plants of the new cultivar as grown outdoors in 17-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Blooms for 10 weeks from July to late September, in The Netherlands.

*Plant type.*—Herbaceous perennial.

*Plant habit.*—Upright.

*Height and spread.*—An average of 70 cm in height and 60 cm in spread.

*Hardiness.*—At least in U.S.D.A Zones 4 to 9.

*Diseases and pests.*—No susceptibility and resistance to diseases or pests has been observed.

*Root description.*—Fibrous and fine, 158C in color.

*Propagation.*—Tissue culture using meristem tissue.

*Growth rate.*—Moderate to high.

*Root development.*—Rooting occurs in about 10 weeks and a young rooted plant can be produced in about 3 months.

Stem description:

*Shape.*—Rounded.

*Stem color.*—145B and marbled with 144B.

*Stem size.*—An average of 49.5 cm in length and 7 mm in diameter.

*Stem strength.*—Very strong.

*Stem aspect.*—Held at an average angle of 15° (0°=vertical).

*Stem surface.*—Moderately covered with very short hairs, an average of 0.4 mm in length colored white; too small and too sparsely present to be measured with RHS-CC.

*Stem number.*—Average of 6 main branches (basal).

*Internode length.*—Average of 4.9 cm.

*Branching.*—Main flowering stem grows from base.

Foliage description:

*Leaf shape.*—Basal leaves and cauline leaves narrow ovate.

*Leaf division.*—Simple.

*Leaf base.*—Basal leaves and cauline leaves attenuate.

*Leaf apex.*—Basal leaves and cauline leaves narrow acute.

*Leaf venation.*—Basal and cauline leaves; 144C in color on upper surface and 145B in color on lower surface.

*Leaf margins.*—Basal leaves and cauline leaves coarsely un-deeply serrate and moderately undulate.

*Leaf attachment.*—Petiolate.

*Leaf arrangement.*—Alternate.

*Leaf size.*—Basal leaves an average of 28.9 cm in length and 8.1 cm in width, cauline leaves an average of 19.3 cm in length and 4.8 cm in width.

*Leaf color.*—Basal and cauline leaves: young upper surface; 144A, young lower surface; 144B, mature upper surface; a color in between 139A and 147A, mature lower surface; NN137B.

*Leaf surface.*—Basal and cauline leaves; upper surface matte, rough to touch, both sides moderately covered with very short strigose hairs an average of 0.3 mm in length and too fine to measure color, lower surface slightly glossy and rough to touch, moderately covered with short strigose hairs an average of 0.3 mm in length and too fine to measure color.

*Petioles.*—V-shaped, basal leaves an average of 14.3 cm in length and 3 mm in diameter, cauline leaves an average of 5 cm in length and 3 mm in diameter, color upper surface 143C towards the proximal end and margined NN137A, color lower surface 144A and fading towards the proximal end to 186B, both surfaces smooth and glabrous.

Flower description:

*Type.*—Terminal capitulum consisting of ray florets and disc florets.

*Capitulum number.*—An average of 3 per stem, 18 per plant.

*Lastingness of inflorescence.*—A few weeks, ray florets self-cleaning.

*Capitulum size.*—Matures to about 6 cm in height and 4.3 cm in diameter, disc diameter is an average of 4.3 cm.

*Inflorescence aspect.*—Held straight on top of peduncles.

*Fragrance.*—None.

*Involucral bracts or phyllary.*—36 spirally arranged in 2 overlapping rows, average of 7 mm in length and 2.5 mm in width, cuneate base, acute apex, ovate to narrow ovate in shape, color upper surface 137A, color lower surface 138A, upper surface texture; smooth, lower surface moderately covered with very short hairs an average of 0.3 mm in length and too fine for color reading.

*Inflorescence buds.*—Flattened globular in shape, immature ray florets near horizontal, in an average angle of 45° to horizontal, an average of 2 cm in length and 5 cm in diameter, color N163B and N163C with immature ray florets 4D, 54C at the base. matte surface texture.

*Peduncle.*—Strong, an average of 12.8 cm in length and 5 mm in diameter, terminal held straight on top of stem, average angle of secondary peduncles: 20° (0°=straight upright), 145B in color and marbled with 144B, surface is slightly to moderately covered with very short strigose hairs an average of 0.3 mm in length; too small and too sparsely present to be measured with color chart.

*Ray florets.*—Rotate around disc in 1 row, average of 25 (varying between 18 and 30) per inflorescence, narrow oblong to oblanceolate in shape, average of 4.0 cm in length and 0.9 cm in width, three-lobed to cleft (deeply emarginated) apex, cuneate base, entire margin, held at an average angle of 40° downward from horizontal, color; upper surface when opening 155A with base 61D, lower surface when opening 155A, base 62B to 62C, upper surface when fully open 150D and tinged at the base 56A, fades to a color between 150D and 145D, lower surface when fully open a color in between 150D and 154D, with base 56B, fading to 150C, surface texture; upper surface glabrous, matte and carinate, lower surface glabrous, slightly glossy and carinate.

*Disk flowers* (*bisexual*).—Numerous, average of 220, arranged spirally on disc, tubular, lower 62.5% fused, held upright to outward aspect, apex is acute, entire margin, average of 1.2 cm in length and 4.5 mm in width, upper and lower surfaces are smooth, glabrous and slightly glossy, color when opening upper surface; 185D with outer tips 185A, base 146D, color when opening lower surface; 185D with outer tips 185A, base 146D, color when fully opened upper and lower surface; tip 180D, midsection 144C, base 144B.

*Disk spines.*—Average of 220, acicular in shape, acute apex, attenuate base, glabrous and glossy surface, color is 53A, fading to 30A at apex, 144A in mid region and 157D at base.

*Receptacle.*—Deltoid in shape, an average of 1.3 cm in height and 1.2 cm in diameter, NN155A in color.

Reproductive organs (present on disk florets only):

*Gynoecium.*—Pistil; average 1; 7 mm in length, style; average 6 mm in length and 145D in color, stigma; unequal decurrent and N186A in color, ovary; 157D in color.

*Androecium.*—Stamens; 5, filaments; 1.5 mm in length and 157D in color, anthers; linear in shape, average 2.5 mm in length, 197A in color, pollen is low in quantity and 17B in color.

*Fruit/seed.*—No seed production has been observed to date.

It is claimed:

1. A new and distinct cultivar of *Echinacea* plant named 'Strawberry and Cream' as herein illustrated and described.

* * * * *